United States Patent [19]

Hafezi

[11] Patent Number: 5,056,525
[45] Date of Patent: Oct. 15, 1991

[54] PROCESS FOR DIAGNOSING SPINAL CONDITIONS

[76] Inventor: Fred F. Hafezi, 3101 Sunrise Ridge, Hacienda Heights, Calif. 91745

[21] Appl. No.: 720,909

[22] Filed: Apr. 8, 1985

Related U.S. Application Data

[63] Continuation of Ser. No. 591,802, Mar. 21, 1984, abandoned, which is a continuation of Ser. No. 181,096, Aug. 25, 1980, abandoned.

[51] Int. Cl.$^5$ ............................................. A61B 10/00
[52] U.S. Cl. ................................... 128/664; 128/736; 128/781
[58] Field of Search ............... 128/736, 781, 742, 744, 128/68, 630, 664

[56] References Cited

U.S. PATENT DOCUMENTS

| | | | |
|---|---|---|---|
| 3,245,402 | 4/1966 | Barnes | 128/664 |
| 4,043,324 | 8/1977 | Shaw | 128/736 |
| 4,173,970 | 11/1979 | Momin | 128/736 |

FOREIGN PATENT DOCUMENTS 692175 10/1930 France ................................ 128/736

OTHER PUBLICATIONS

Barr, The Human Nervous System, Harper and Row, N.Y., 1972, pp. 75–77.
"Peripheral Circulation," AGA Thermovision Medical Application, AGA Publication 556/048, 1973.
DeGowin, Bedside Diagnostic Examinations; 2nd Ed., Macmillan Co., London, 1969, pp. 790–792.
"Proven in the World's Great Hospitals," AGA Corp., Secaucus, N.J., 1973.
"Thermographing in Rheumatic Diseases", AGA publication 556,089, 1973.

Primary Examiner—Kyle L. Howell
Assistant Examiner—J. Hanley
Attorney, Agent, or Firm—Burns, Doane, Swecker & Mathis

[57] ABSTRACT

A process for diagnosing abnormal spinal conditions. The process utilizes the step of placing the patient in a draft-free room and uniformly spraying the patient with an evaporative liquid. After a waiting period, the surface skin temperature is measured and areas of above or below normal skin temperature are mapped.

5 Claims, 2 Drawing Sheets

General Indications of Zones

Unmarked Body

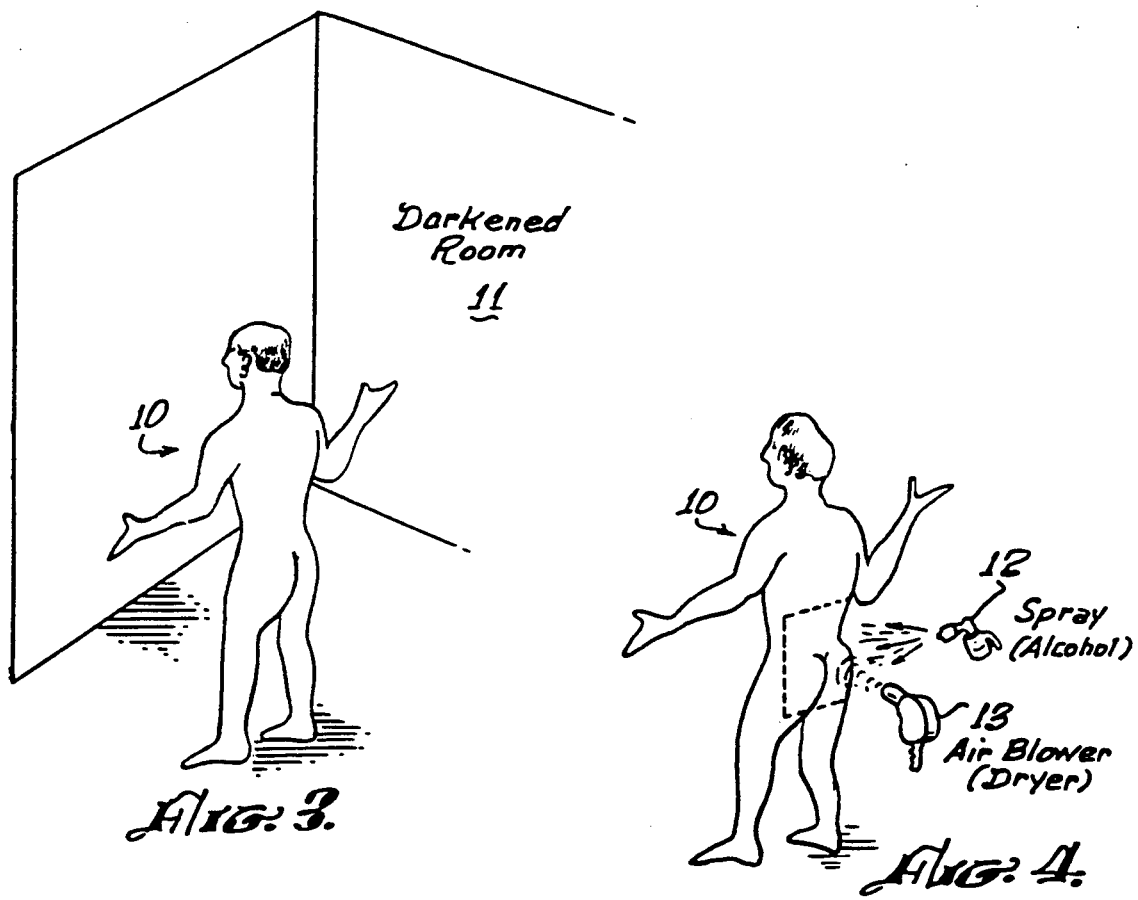
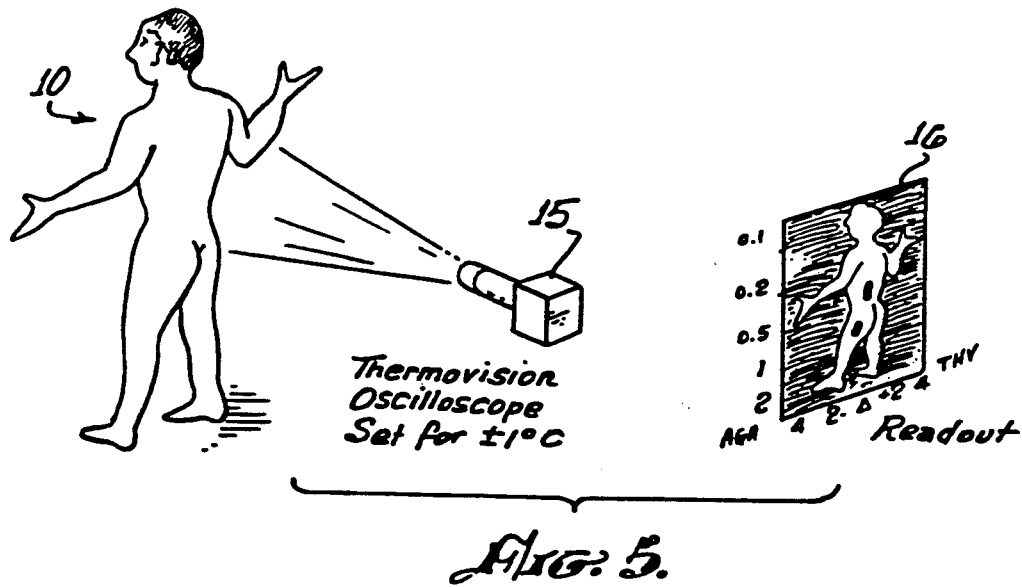

PROCESS FOR DIAGNOSING SPINAL CONDITIONS

CROSS-REFERENCE TO RELATED APPLICATIONS

This application is a continuation to my earlier co-pending application, U.S. Ser. No. 591,802, filed Mar. 21, 1984, now abandoned, which is a continuation of U.S. Ser. No. 181,096, filed Aug. 25, 1980 now abandoned. Said applications are expressly incorporated by reference herein in their entirety and relied upon.

BACKGROUND OF THE DISCLOSURE

One of the most persistent problems in medical diagnostics is the accurate diagnosis and location of spinal injuries or abnormalities. In many instances, such abnormalities are not visible by the use of x-rays and, instead, subjective evidence must be evaluated. The patient complains of pain but the source and even the existence and extent of such pain is difficult to determine.

A very common source of lengthy lawsuits if this very problem, namely whether or not the injured party is in fact in pain or merely a malingerer. In the typical automobile whiplash case, experts for both sides testify at length as to the existence or absence of injury without the benefit of objective findings, and injustice often results.

The widespread use of x-rays in diagnostics is receiving increasingly negative publicity because of the potential harm that this technique entails. Thus, a diagnostic technique which does not require the use of x-rays would be highly beneficial.

A process known as "thermography" has been developed and has found use in the detection of breast cancer and tumors. This same process is also utilized industrially to locate cracks and other defects in pipes and other articles. The process is capable of locating zones of abnormal temperature.

SUMMARY OF THE INVENTION

It is thus an object of the present invention to devise a process for providing objective evidence of spinal injuries and abnormalities without the harmful use of x-rays and furthermore of locating such abnormalities where x-rays are not effective.

The present invention is for a process for diagnosing abnormal spinal conditions comprising the steps of placing the patient whose spinal abnormality is to be diagnosed in a draft-free room free from sources of radiant heat which would tend to elevate the temperature of the surface of the skin. An area of the patient is then uniformly sprayed with an evaporative liquid such as a solution of ethanol and the liquid is allowed to evaporate cooling the skin surface. The patient then waits for about five to ten minutes while the skin surface temperature tends to return to normal. The surface temperature of the skin is then carefully measured by a technique such as thermography and the areas of differential skin surface temperature are mapped to show areas where the temperature differs significantly from the mean skin temperature. The location of the differential skin surface temperature areas and the fact of their being either above or below the mean skin temperature is then used to diagnose the spinal condition.

BRIEF DESCRIPTION OF THE DRAWINGS

FIG. 3 is a perspective view showing one of the steps of the process of the present invention.

FIG. 4 is a perspective view showing one of the steps of the process of the present invention.

FIG. 5 is a perspective view showing one of the steps of the process of the present invention.

DESCRIPTION OF THE PREFERRED EMBODIMENTS

Figure 1:
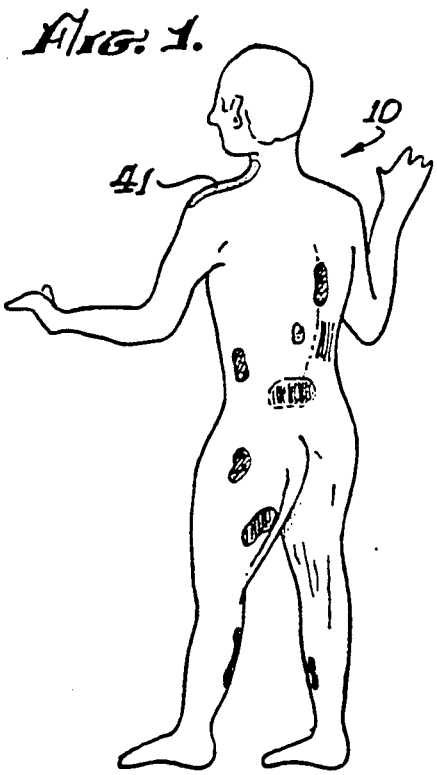
FIG. 1 is a perspective view of the back side of a patient showing various areas of abnormal temperatures associated with different spinal abnormalities.

The process of the present invention is carried out by providing a uniform heat loss about the patient's body and, after the temperature of the patient has begun to return to normal, a temperature scan is made and the differential skin surface temperatures are observed. The first step, thus, involves the careful cooling of the patient's skin (as shown in FIG. 3) which is most readily accomplished by having the patient 10 stand naked in a draft-free, darkened room 11 having a minimal light source. There should be no source of radiant or other heat to causae an increase in skin temperature distorting the outcome of the testing procedure.

The location of any bruises, rashes, sunburn, boils, infections or other skin disruptions is noted and recorded. It must be recognized that conditions such as sunburn or rash will give rise to the possibility of erroneous results.

The part of the body 10 to be examined is uniformly sprayed with an evaporative liquid from a spray gun 12 such as a solution of ethyl alcohol and dried by an air blower 13 with cold air. Other evaporative substances may be used in the place of ethyl alcohol with consideration being given to dermatological reactions and patient comfort. Other means of cooling the skin surface temperature such as immersion could be used, but patient comfort favors spraying with an evaporative substance such as ethyl alcohol.

Parts of the body such as legs and arms should not touch each other since this would affect the skin surface temperature. The patient is told to sit or stand relaxed without tightening his muscles since this too affects skin surface temperature. After a period of time sufficient to permit the skin surface temperature to return in part to normal, the skin surface temperature is measured. This is depicted schematically in FIG. 5. The amount of time after the cooling step and before measurement of the temperature will vary depending upon the room temperature, but generally from three to fifteen minutes is appropriate and from five to ten minutes is preferred and at least three minutes is required for meaningful results to show. An instrument depicted at 15 and 16 measures surface temperature differences.

A preferred method of locating areas of skin temperature differences is the use of an instrument known under the name "Thermovision Oscilloscope" and specifically a Model 680AGA Thermovision Oscilloscope. The grey scale for the black and white screen is adjusted to span two degrees centigrade and, utilizing the isotherm mode, the knob is turned to scan the skin temperature up to four degrees above and four degrees below the mean skin temperature. Generally, the areas are mapped where the temperature differs from the mean skin temperature by at least one degree centigrade. For certain conditions, areas of the skin will be above the mean skin temperature and for other conditions, areas will be below mean skin temperature.

Figure 2:
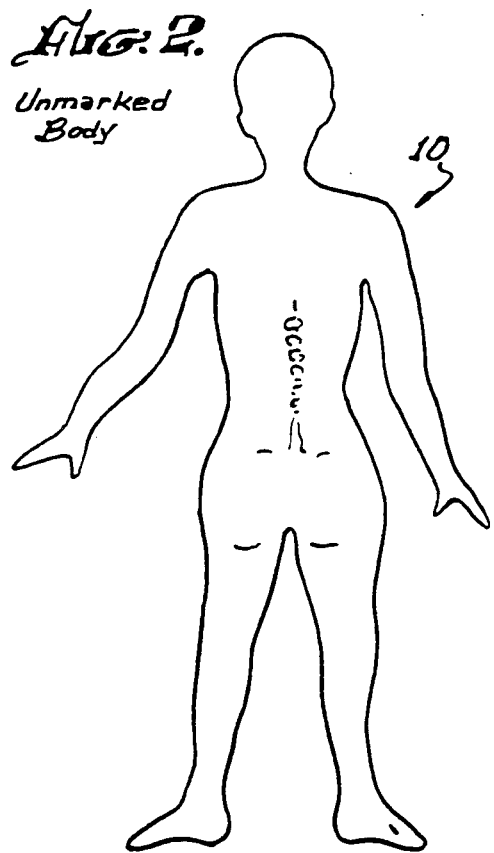
FIG. 2 is the back side of a patient.

Various typical areas of skin temperature differences are shown in FIG. 1 of the drawings although a patient would only have one or two such areas. An unmarked uniform temperature body is shown in FIG. 2. Various patterns of temperature differences are shown in FIG. 2a through 2h.

Figure 2A:
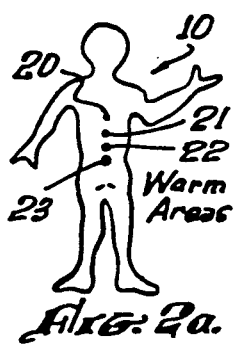
FIG. 2a through 2h are back elevational views depicting temperature patterns of different patients.
Figure 2B:
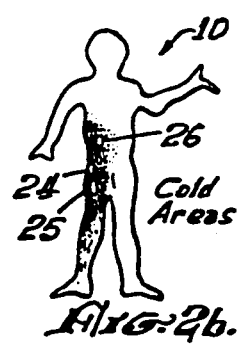
Figure 2C:
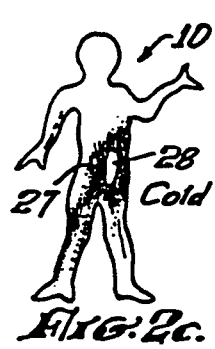

As indicated by reference character 23 in FIG. 2a, an L5-S1 disc herniation presents a well circumscribed round hot spot in the area over the L5-S1 disc. Similarly the L4-S5 disc and L3-L4 disc herniations show as hot spots over these areas indicated by reference characters 22 and 21 respectively. A high lumbar disc herniation is hot area 20.

In contrast, an L4-L5 internal disc disruption shows as a cold well circumscribed spot over the upper outer quadrant of the buttocks toward the affected side. This is indicated by reference character 24 in FIG. 2b. Frequently, the patient feels pain at that site which represents a cold spot of varying intensity over the lower inner quadrant of the buttocks indicated by reference character 25. An L3-L4 disc disruption presents a cold oval or round area over the flank as represented by reference character 26 in FIG. 2b.

Facet synovites is represented by a paramedian assymetrical hot spot of varying intensity directly over the facet joint at the level of the spine involved. This is shown by reference character 27 in FIG. 2c. Lumbosacral muscle sprain or spasm shows a rectangular cold area 28 along the spine arising from the iliac crest shown in FIG. 2c.

Figure 2D:
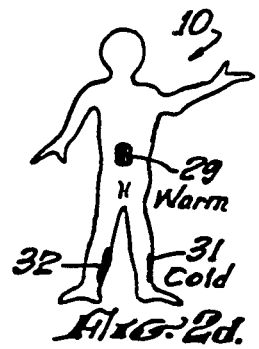
Figure 2E:
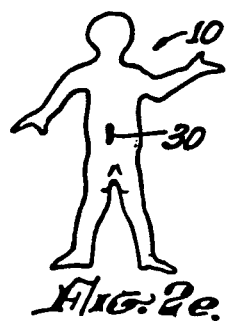

Contusion of the low back presents a diffuse large area of heat covering most of the low back as indicated by reference character 29 in FIG. 2d. Low back ligamentous sprain is an oblong warm area along the interspinous ligament as indicated by reference character 30 in FIG. 2e.

Figure 2F:
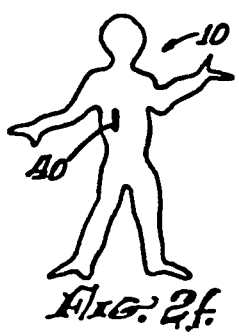
Figure 2G:
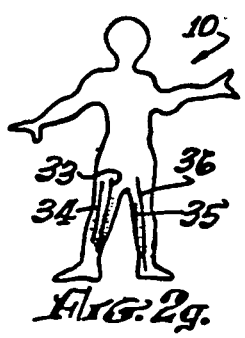

Lumbosacral radiculitis presents cold streaks, bars or spots in the legs as follows: S1 radiculitis is a cold bar limited to the lateral lower half of the calf as shown by reference character 31 in FIG. 2d. L5 radiculitis presents a cold bar medial in the lower half of the calf reference character 32 in FIG. 2d. L5 root damage reference character 33, S1 root damage reference character 34 and l4 nerve root reference character 35 are all shown in FIG. 2g. S1 root damage reference character 36 is also shown in FIG. 2g. Alternate appearance of radiculitis lumbosacral nerve roots are shown in FIG. 2h where S1 root damage is shown by reference character 45 and L5 root damage at 4b (both are cold areas).

Figure 2H:
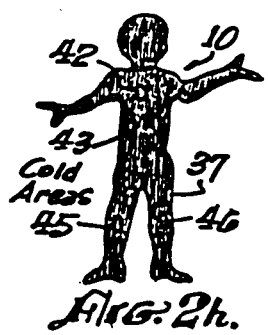

Fourth lumbar nerve root lesions show a cold area over the lateral distal half of the thigh as shown by reference character 37 in FIG. 2h. Parathoracic muscle sprain reference character 40 is shown in FIG. 2f.

A warm area reference character 41 in FIG. 1 represents a cervical sprain and a cold area reference character 42 indicates C7 disc damage. Cold areas reference character 43 in FIG. 2h indicates C5 and C6 disc disease. Cold areas in the shoulder to upper limbs represent cervical radiculitis according to dermotomal distribution.

It can, thus, be readily seen that the method of the present invention is capable of diagnosing abnormal spinal conditions without resorting to potentially harmful x-rays and with a minimum of discomfort to the patient. Certain precautions should be taken during the diagnostic technique to reduce the possibility of false reading. In addition to the sunburn and other skin disruptions mentioned above, voluntary tightening of the back and neck muscles can cause erroneous readings. Similarly, a heat source such as a lamp can distort the normal constant cooling which is required. A draft or breeze in the diagnosis room can also cause a cooling and the patient's use of a linament or topical skin medication will likewise affect skin surface temperature and distort results. Rubbing of the skin surface increases skin surface temperature and should be avoided.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. A process for diagnosing abnormal spinal conditions comprising the steps of:

placing the patient whose spinal abnormality is to be diagnosed in a standing position in a room free from random draft, and free from a source of radiant heat in order to provide a uniform heat loss about the patient's body;

spraying each side of the patient's skin with an evaporative liquid while the patient's legs are not touching each other and the patient's arms are not touching any part of the patient's body;

uniformly blowing room temperature air on the patient's skin to allow the evaporative liquid to evaporate thereby cooling the skin surface;

waiting while the patient stands in a relaxed manner in the room for a period of from three to fifteen minutes to permit the skin surface temperature to return in part to normal;

measuring the skin surface temperature to determine the mean skin temperature;

mapping the areas of differential skin surface temperature about the patient's torso and limbs including areas remote from the site of pain where said temperature differs from the mean skin temperature by at least one degree centigrade above or below said mean skin temperature to locate a pattern characteristic of a particular injury; and determining the area of the spinal abnormality by comparing the map of the areas of differential skin surface temperature with the peripheral distribution of particular sympathetic sensory nerves near the spinal abnormality.

2. The method of claim 1 wherein the skin surface temperature differs by about two degrees centigrade.

3. The process of claim 1 wherein the waiting time is from five to ten minutes.

4. The process of claim 1 wherein ethanol is the evaporative liquid.

5. The process of claim 1 wherein a Thermovision Oscilloscope is used to map the skin surface temperature differences.

* * * * *